(12) United States Patent
Jallon (10) Patent No.: US 8,977,522 B2
(45) Date of Patent: Mar. 10, 2015

(54) SYSTEM AND METHOD FOR OBSERVING A PERSON'S WALKING ACTIVITY

(75) Inventor: Pierre Jallon, Grenoble (FR)

(73) Assignees: Commisariat a l'Energie Atomique et aux Energies Alternatives, Paris (FR); Movea SA, Grenoble (FR)

( * ) Notice: Subject to any disclaimer, the term of this patent is extended or adjusted under 35 U.S.C. 154(b) by 300 days.

(21) Appl. No.: 13/258,799

(22) PCT Filed: Mar. 29, 2010

(86) PCT No.: PCT/EP2010/054130
§ 371 (c)(1),
(2), (4) Date: Dec. 6, 2011

(87) PCT Pub. No.: WO2010/112469
PCT Pub. Date: Oct. 7, 2010

(65) Prior Publication Data
US 2012/0078594 A1    Mar. 29, 2012

(30) Foreign Application Priority Data

Mar. 31, 2009 (FR) .................... 09 52012

(51) Int. Cl.
*G06F 17/10* (2006.01)
*A63B 24/00* (2006.01)
(Continued)

(52) U.S. Cl.
CPC ............ *A63B 24/0062* (2013.01); *A61B 5/112* (2013.01); *A63B 24/0006* (2013.01); *A61B 5/7264* (2013.01); *A63B 23/0458* (2013.01);
(Continued)

(58) Field of Classification Search
USPC .......................................... 703/2
See application file for complete search history.

(56) References Cited

U.S. PATENT DOCUMENTS

2005/0177080 A1* 8/2005 Yasuhara et al. ............... 602/16
2006/0046910 A1* 3/2006 Rastegar et al. ............... 482/91
(Continued)

FOREIGN PATENT DOCUMENTS

EP    1 547 567 A1    6/2005
EP    2 011 552 A1    1/2009

OTHER PUBLICATIONS

Coley et al.: Stair climbing detection during daily physical activity using a miniature gyroscope, Gait & Posture 22 (2005) pp. 287-294.*
Chen et al.; Human Abnormal Gait Modeling via Hidden Markov Model; Proceedings of the 2007 International Conference on Information Acquisition; 2007; pp. 517-522.*
Pappas et al.; A Reliable Gait Phase Detection System; IEEE Transactions on Neural Systems and Rehabilitation Engineering, vol. 9, No. 2, Jun. 2001; pp. 113-125.*

(Continued)

*Primary Examiner* — Hugh Jones
(74) *Attorney, Agent, or Firm* — Stroock & Stroock & Lavan LLP (57) ABSTRACT

A system for observing a walking activity of a person comprises a device (DISP) adapted for delivering at output, for a footstep of the person, a first difference of angular speeds of the corresponding tibia between the instant at which the heel of the foot is planted and the instant at which the foot is laid flat, a second difference of angular speeds of the corresponding tibia between the instant at which the heel of the foot is planted and the instant at which the last toe of the foot is lifted, and an angular speed of the corresponding tibia at the instant at which the foot is laid flat. The system comprises analysis means (AN) for analyzing the signals delivered by the device and adapted for determining a type of walking of the user as a function of time by using a hidden Markov model with N states corresponding respectively to N types of walking.

25 Claims, 2 Drawing Sheets

(51) Int. Cl.
*A61B 5/11* (2006.01)
*A61B 5/00* (2006.01)
*A63B 23/04* (2006.01)
*A63B 69/00* (2006.01)

(52) U.S. Cl.
CPC ..... *A63B 69/0028* (2013.01); *A63B 2024/0012* (2013.01); *A63B 2024/0071* (2013.01); *A63B 2220/22* (2013.01); *A63B 2220/34* (2013.01)
USPC ............................................................ 703/2

(56) References Cited

U.S. PATENT DOCUMENTS

2006/0284979 A1* 12/2006 Clarkson ...................... 348/143
2008/0039756 A1* 2/2008 Thorsteinsson et al. ........ 602/23

OTHER PUBLICATIONS

Lan et al.; A Unified Spatio-Temporal Articulated Model for Tracking; Proceedings of the 2004 IEEE Computer Society Conference on CVPR (vol. 1); 2004; pp. I-722-I-7291.*
Tong et al.; A practical gait analysis system using gyroscopes; Medical Engineering & Physics 21 (1999) 87-94.*
Bhatia et al.; 3D Human Limb Detection using Space Carving and Multi-view Eigen Models; Proceedings of the 2004 IEEE Computer Society Conference on Computer Vision and Pattern Recognition Workshops (CVPRW'04); pp. 1-5.*
Coley et al.: Stair climbing detection during daily physical activity using a miniature gyroscope; Gait & Posture 22 (2005) 287-294.*
International Search Report and Written Opinion dated Jul. 2, 2010, issued in counterpart International Application No. PCT/EP2010/054130.

* cited by examiner

SYSTEM AND METHOD FOR OBSERVING A PERSON'S WALKING ACTIVITY

CROSS-REFERENCE TO RELATED APPLICATIONS

This application is a national phase application under §371 of PCT/EP2010/054130, filed Mar. 29, 2010, which claims priority to French Patent Application No. 0952012, filed Mar. 31, 2009, both of which are incorporated herein in their entirety.

FIELD OF THE INVENTION

The present invention pertains to a system and a method for observing a person's walking activity, or—for observing a person's movement by a mode of locomotion comprising a series of paces.

BACKGROUND OF THE INVENTION

Systems for analyzing the motion of people are becoming increasingly widespread in the biomedical sector, notably for analyzing a person's physical activity.

The detection of a person's walking activity is an item of information which makes it possible, for example, to estimate a person's energy expenditure, to evaluate a person's level of sedentariness, or to estimate the quality or the loss of functional capacity after a surgical intervention or a medicinal treatment.

The document "Stair climbing detection during daily physical activity using a miniature gyroscope" by Brian Coley, Bijan Najafi, Anisoara Paraschiv_Ionescu, and Kamiar Aminian, published in Gait and Posture in 2005, pertains to the detection of stair climbing and descent with the aid of a gyroscope. For this purpose, the system estimates the various characteristic instants of a walking cycle.

SUMMARY OF THE INVENTION

Embodiments of the present invention are aimed at allowing qualitative analysis of a person's walking activity, which may be particularly useful for accurately monitoring a person's activity.

Hence, there is proposed, according to one aspect of the invention, a system for observing a walking activity of a person, comprising a device adapted for delivering at output, for a footstep of the person, a first difference of angular speeds of the corresponding tibia between the instant at which the heel of the foot is planted and the instant at which the foot is laid flat, a second difference of angular speeds of the corresponding tibia between the instant at which the heel of the foot is planted and the instant at which the last toe of the foot is lifted, and an angular speed of the corresponding tibia at the instant at which the foot is laid flat. The embodiment system comprises, furthermore, analysis means for analyzing the signals delivered by the device and adapted for determining a type of walking of the user as a function of time by using a hidden Markov model with N states corresponding respectively to N types of walking.

Such a system makes it possible, at reduced cost, to observe and to determine accurately the walking activity of a person.

According to one embodiment, the probability density $p_x$ $\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{-\frac{(\underline{x}(n)-\underline{\mu})^T \Sigma^{-1} (\underline{x}(n)-\underline{\mu})}{2}}$$

in which:
$\underline{x}(n)$ represents the column vector with three components representative of signals transmitted by the device;
$\underline{\mu}$ represents a column vector with three components, representative of the state of the hidden Markov model corresponding to said type of walking; and
$|\Sigma|$ represents the absolute value of the determinant of a diagonal matrix $\Sigma$ of dimension 3 representative of the state of the hidden Markov model corresponding to said type of walking.

The use of a hidden Markov model such as this makes it possible to accurately distinguish the type of walking employed in real time.

In one embodiment, the probability density of correspondence between the signals delivered by the device and a state of the hidden Markov model representing a type of walking is defined by a linear combination of said first expressions for the probability densities of the set of types of walking, the sum of the coefficients of said linear combination being equal to 1.

This makes it possible to substantially improve the accuracy of the results.

According to one embodiment, the analysis means are adapted for determining the type of walking of the user from among a set of at least two types of walking from among walking on the flat, walking down a descent, walking up a climb, climbing a staircase, descending a staircase.

Thus, the invention makes it possible to distinguish any type of walking from among these conventional types of walking.

In one embodiment, for walking on the flat, the three components $\mu_1$, $\mu_2$, $\mu_3$ of the column vector $\underline{\mu}$ are such that $\mu_1 \in [-1.2; -1]$, $\mu_2 \in [0.25; 0.35]$, and $\mu_3 \in [-0.3; -0.2]$, and the three diagonal components $\Sigma_1$, $\Sigma_2$, $\Sigma_3$ of the diagonal matrix $\Sigma$ are such that $\Sigma_1 \in [10^{-3}; 510^{-2}]$, $\Sigma_2 \in [10^{-4}; 510^{-3}]$, and $\Sigma_3 \in [10^{-4}; 510^{-2}]$.

According to one embodiment, for walking down a descent, the three components $\mu_1$, $\mu_2$, $\mu_3$ of the column vector $\underline{\mu}$ are such that $\mu_1 \in [-1.4; -1]$, $\mu_2 \in [0.05; 0.25]$, and $\mu_3 \in [-0.7; -0.2]$, and the three diagonal components $\Sigma_1$, $\Sigma_2$, $\Sigma_3$ of the diagonal matrix $\Sigma$ are such that $\Sigma_1 \in [10^{-3}; 510^{-2}]$, $\Sigma_2 \in [10^{-3}; 10^{-2}]$, and $\Sigma_3 \in [10^{-4}; 510^{-2}]$.

In one embodiment, for walking up a climb, the three components $\mu_1$, $\mu_2$, $\mu_3$ of the column vector $\underline{\mu}$ are such that $\mu_1 \in [-1.1; -0.2]$, $\mu_2 \in [0.1; 0.2]$, and $\mu_3 \in [-1.2; -0.6]$, and the three diagonal components $\Sigma_1$, $\Sigma_2$, $\Sigma_3$ of the diagonal matrix $\Sigma$ are such that $\Sigma_1 \in [10^{-3}; 510^{-2}]$, $\Sigma_2 \in [10^{-3}; 10^{-2}]$, and $\Sigma_3 \in [10^{-3}; 510^{-2}]$.

According to one embodiment, for climbing a staircase, the three components $\mu_1$, $\mu_2$, $\mu_3$ of the column vector $\underline{\mu}$ are such that $\mu_1 \in [-0.4; -0.15]$, $\mu_2 \in [0; 0.2]$, and $\mu_3 \in [-0.7; -0.4]$, and the three diagonal components $\Sigma_1$, $\Sigma_2$, $\Sigma_3$ of the diagonal matrix $\Sigma$ are such that $\Sigma_1 \in [10^{-2}; 10^{-1}]$, $\Sigma_2 \in [510^{-3}; 510^{-2}]$, and $\Sigma_3 \in [10^{-2}; 10^{-1}]$.

In one embodiment, for descending a staircase, the three components $\mu_1$, $\mu_2$, $\mu_3$ of the column vector $\underline{\mu}$ are such that $\mu_1 \in [-0.8; -0.6]$, $\mu_2 \in [-0.3; -0.1]$, and $\mu_3 \in [-0.4; -0.25]$, and the three diagonal components $\Sigma_1, \Sigma_2, \Sigma_3$ of the diagonal matrix $\Sigma$ are such that $\Sigma_1 \in [10^{-3}; 10^{-2}], \Sigma_2 \in [10^{-4}; 10^{-3}]$, and $\Sigma_3 \in [10^{-4}; 10^{-3}]$.

According to one embodiment, the probabilities P, of said hidden Markov model, of switching between two states representing respectively one of said types of walking are such that:

P(state$_i$,state$_j$)$\in$[0.5; 0.9999], when i is different from j; and
P(state$_i$,state$_j$)$\in$[0; 0.5], when i is equal to j.

The accuracy of the system is thus improved.

In one embodiment, said analysis means are fastened or remote with respect to the device, and the device comprises wired or wireless transmission means for transmitting its measurements to said analysis means.

Thus, numerous embodiments may be envisaged.

According to one embodiment, the system comprises, furthermore, display means fastened to the device and/or remote display means.

Thus, the results of analyzing the walking activity of the user may be viewed directly, or indeed analyzed and viewed on a larger external screen, for example of a laptop computer which can comprise the analysis means.

According to one embodiment, the device comprises a magnetometer, and/or an accelerometer, and/or a gyrometer for delivering its output signals.

According to another aspect of the invention, there is also proposed a method for observing a walking activity of a person, on the basis, during a footstep, of signals representing a first difference of angular speeds of the corresponding tibia between the instant at which the heel of the foot is planted and the instant at which the foot is laid flat, a second difference of angular speeds of the corresponding tibia between the instant at which the heel of the foot is planted and the instant at which the last toe of the foot is lifted, and an angular speed of the corresponding tibia at the instant at which the foot is laid flat. Said signals are analyzed to determine a type of walking of the user as a function of time by using a hidden Markov model with N states corresponding respectively to N types of walking.

BRIEF DESCRIPTION OF THE DRAWINGS

The invention will be better understood on studying a few embodiments described by way of wholly non-limiting examples and illustrated by the appended drawings in which.

DETAILED DESCRIPTION OF THE INVENTION

In all the figures, the elements having the same references are similar.

Figure 1:
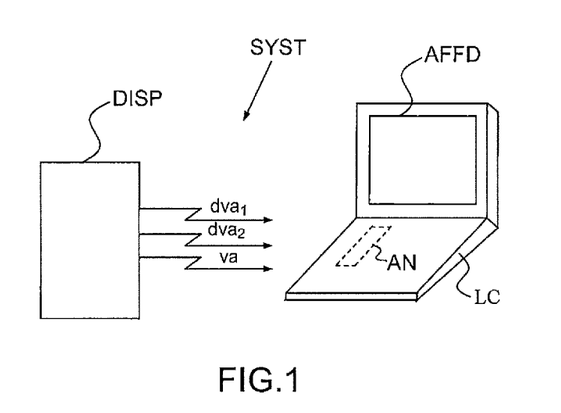
FIGS. 1 and 2 illustrate two embodiments of systems according to one aspect of the invention.

As illustrated in FIG. 1, the embodiment system SYST for observing a walking activity of a person comprises a device DISP adapted for delivering as output, for a footstep of the person, a first difference $dva_1$ of angular speeds of the corresponding tibia between the instant at which the heel of the foot is planted and the instant at which the foot is laid flat, a second difference $dva_2$ of angular speeds of the corresponding tibia between the instant at which the heel of the foot is planted and the instant at which the last toe of the foot is lifted, and an angular speed va of the corresponding tibia at the instant at which the foot is laid flat.

Such a device DISP is for example described in French patent application FR 08/00571 and comprises a magnetometer intended to be fixed to a tibial segment of the person so as to generate a signal representative of at least one projection in a sagittal plane of an ambient magnetic field in which he is immersed, and a module for processing the signal so as to identify characteristic instants and/or phases of the walking of the person on the basis of the signal generated by the magnetometer. By assuming that the person moves in a plane, that is to say the person walks in a straight line, it is possible to estimate the angular speed of the tibia on the basis of the magnetometer. This item of information can also be obtained directly on the basis of a gyrometer. On the basis of this item of information, the characteristic instants of the walking cycle may be deduced as described in the document "Stair climbing detection during daily physical activity using a miniature gyroscope" by Brian Coley, Bijan Najafi, Anisoara Paraschiv_Ionescu, and Kamiar Aminian.

As a variant, the device DISP can comprise an accelerometer and/or a gyrometer, and/or a magnetometer for generating its output signals.

The output signals of the device DISP are transmitted, for example by wireless link, to a remote analysis module AN, for example integrated into a laptop computer LC furnished with a large display screen AFFD.

Figure 2:
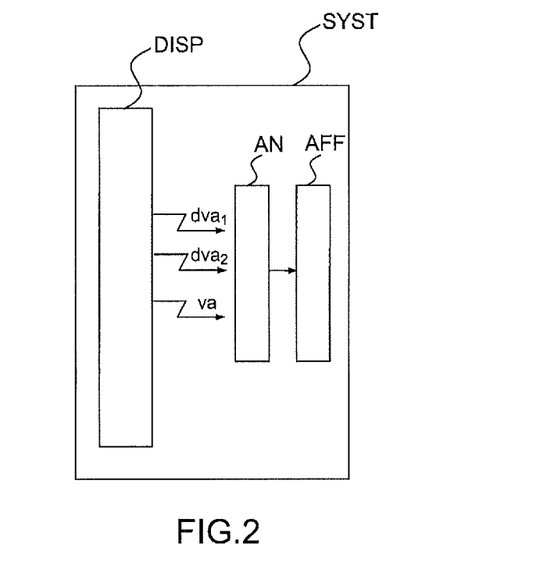

As a variant, as illustrated in FIG. 2, the analysis module may be fastened to the device DISP, and the latter may be furnished with a display screen AFF.

In the subsequent description, the wholly non-limiting example dealt with is a system according to one aspect of the invention, in which the analysis module AN is adapted for determining the type of walking of the user as a function of time by using a hidden Markov model with 5 states (N=5) corresponding respectively to walking on the flat (state 1), walking down a descent (state 2), walking up a climb (state 3), climbing a staircase (state 4), and descending a staircase (state 5).

These three signals provided by the device DISP are denoted in the form of a three-dimensional vector: $\underline{x}(n)=[x_1(n), x_2(n), x_3(n)]^T=[dva_1(n), dva_2(n), va(n)]^T$, in which n represents the index of the sample at the frequency provided by the device DISP, and x1, x2, and x3 represent the values of the signals corresponding to the three signals delivered by the device DISP, i.e. dva1, dva2, and va.

The probability density $p_x\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{-\frac{(\underline{x}(n)-\underline{\mu})^T \Sigma^{-1} (\underline{x}(n)-\underline{\mu})}{2}}$$

in which:

$\underline{x}(n)$ represents the column vector with components of the three signals transmitted by the device DISP;

$\underline{\mu}$ represents a column vector with three components, representative of the state of the hidden Markov model corresponding to said type of walking; and $|\Sigma|$ represents the absolute value of the determinant of a diagonal matrix $\Sigma$ of dimension 3 representative of the state of the hidden Markov model corresponding to said type of walking.

The five types of walking of the example considered are defined by the following parameters corresponding to the first expression for the probability density $p_{x,k}$ associated with the state k:

walking on the flat (state 1 of the hidden Markov model):

$$\mu = [1.4421; -1.8292; -0.9000]^T \text{ and } \Sigma = \begin{bmatrix} 0.145 & 0 & 0 \\ 0 & 0.40 & 0 \\ 0 & 0 & 0.05 \end{bmatrix}$$

walking down a descent (state 2 of the hidden Markov model):

$$\mu = [1.9393; -1.0854; -0.6676]^T \text{ and } \Sigma = \begin{bmatrix} 0.041 & 0 & 0 \\ 0 & 0.073 & 0 \\ 0 & 0 & 0.1 \end{bmatrix}$$

walking up a climb (state 3 of the hidden Markov model):

$$\mu = [2.88; 0.24; -0.34]^T \text{ and } \Sigma = \begin{bmatrix} 0.95 & 0 & 0 \\ 0 & 0.24 & 0 \\ 0 & 0 & 0.45 \end{bmatrix}$$

climbing a staircase (state 4 of the hidden Markov model):

$$\mu = [1.14; -2.19; 0.46]^T \text{ and } \Sigma = \begin{bmatrix} 0.39 & 0 & 0 \\ 0 & 0.60 & 0 \\ 0 & 0 & 0.16 \end{bmatrix}$$

descending a staircase (state 5 of the hidden Markov model):

$$\mu = [0.70; -1.0; -0.35]^T \text{ and } \Sigma = \begin{bmatrix} 0.15 & 0 & 0 \\ 0 & 0.10 & 0 \\ 0 & 0 & 0.05 \end{bmatrix}$$

The probability densities of switching $P(\text{state}_i/\text{state}_j)$ from one state $\text{state}_i$ corresponding to a type of walking of the hidden Markov model to another state $\text{state}_j$ corresponding to a type of walking of the hidden Markov model are the following, chosen so as to ensure good stability of the system:

| $P(\text{state}_i/\text{state}_j)$ | $\text{state}_i$ = 1 (walking on the flat) | $\text{state}_i$ = 2 (walking down a descent) | $\text{state}_i$ = 3 (walking up a climb) | $\text{state}_i$ = 4 (climbing a staircase) | $\text{state}_i$ = 5 (descending a staircase) |
|---|---|---|---|---|---|
| $\text{state}_j$ = 1 (walking on the flat) | 0.99 | 0.0025 | 0.0025 | 0.0025 | 0.0025 |
| $\text{state}_j$ = 2 (walking down a descent) | 0.0025 | 0.99 | 0.0025 | 0.0025 | 0.0025 |
| $\text{state}_j$ = 3 (walking up a climb) | 0.0025 | 0.0025 | 0.99 | 0.0025 | 0.0025 |
| $\text{state}_j$ = 4 (climbing a staircase) | 0.0025 | 0.0025 | 0.0025 | 0.99 | 0.0025 |
| $\text{state}_j$ = 5 (descending a staircase) | 0.0025 | 0.0025 | 0.0025 | 0.0025 | 0.99 |

Such a system makes it possible to distinguish the changes between the various types of walking of a user. The switching probabilities are chosen sufficiently close to 1 so as to ensure good stability of the system. Indeed, it is desirable to observe for at least a certain duration that the nature of the signals has changed in order for the analysis module AN to decide that the type of walking has changed.

It is possible to substantially improve the performance of the system by defining the probability density of correspondence between the signals delivered by the device DISP and a state of the hidden Markov model representing a type of walking by a linear combination of said first expressions for the probability densities of the set of types of walking, the sum of the coefficients of said linear combination being equal to 1.

We thus write, for state i of the hidden Markov model:

$$P_X^i(\underline{x}(n)) = \sum_{k=1}^{5} \alpha_{i,k} p_{X,k}(\underline{x}(n))$$

$p_{X,k}(\underline{x}(n))$ being said first expression for the probability density $p_{x,k}$ associated with the state k.

$\alpha_{i,k}$ being a weighting coefficient $$\text{with } \sum_{k=1}^{5} \alpha_{i,k} = 1$$

In this example, the following values have been used for the weighting coefficients:

| | k = 1 (walking on the flat) | k = 2 (walking down a descent) | k = 3 (walking up a climb) | k = 4 (climbing a staircase) | k = 5 (descending a staircase) |
|---|---|---|---|---|---|
| $\alpha_{1,k}$ | 0.9 | 0 | 0 | 0 | 0.1 |
| $\alpha_{2,k}$ | 0.025 | 0.9 | 0.025 | 0.0025 | 0.0025 |
| $\alpha_{3,k}$ | 0.025 | 0.025 | 0.9 | 0.025 | 0.0025 |
| $\alpha_{4,k}$ | 0.025 | 0.025 | 0.025 | 0.9 | 0.0025 |
| $\alpha_{5,k}$ | 0 | 0 | 0 | 0.03 | 0.97 |

The analysis module AN determines, on the basis of the input signals and of the hidden Markov model such as defined, the most probable sequence of states (types of walking), according to conventional methods, for example by calculating for the set of possible sequences of states the associated probability having regard to the signal observed and by retaining the most probable sequence, such as are described for example in the document "An introduction to hidden Markov models" by L. R. Rabiner and B. H. Juang, IEEE ASSP Magazine, January 1986, or in the book "Inference in Hidden Markov Models" by Cappé, Moulines and Ryden from Springer, from the series "Springer series in statistics".

Figure 3:
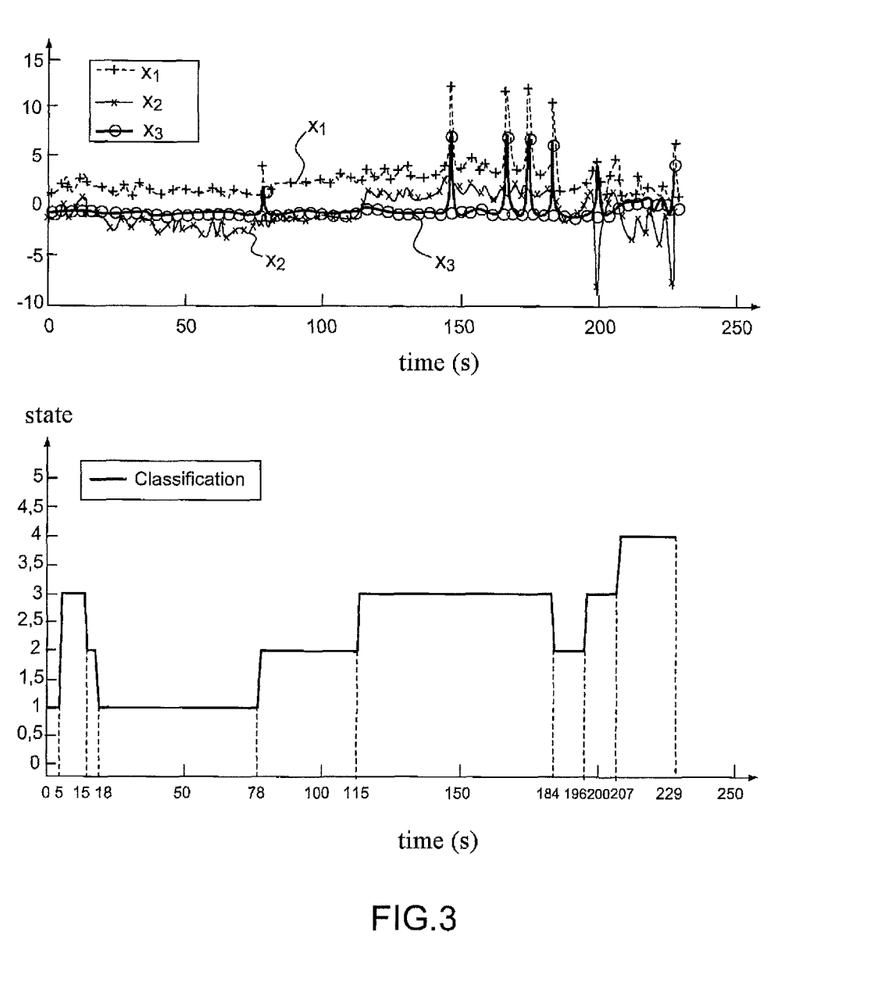
FIG. 3 illustrates two examples of results of a system according to one aspect of the invention.

FIG. 3 illustrates an exemplary recording of a walking session of a user of the system, within the first graph the three curves representing the values of $x_1$, $x_2$ and $x_3$ equal respectively to $dva_1$, $dva_2$ and $va$ transmitted by the device DISP, as a function of time, and in the second graph, the walking state of the patient determined by the system SYST.

In this example, the user has walked on the flat (state 1) for 5 seconds, has then walked up a climb (state 3) for 10 seconds, has then walked down a descent (state 2) for 3 seconds, has then walked on the flat (state 1) for 60 seconds, has then walked down a descent (state 2) for 37 seconds, has then walked up a climb (state 3) for 69 seconds, has then walked down a descent (state 2) for 12 seconds, has then walked up a climb (state 3) for 11 seconds, and has then climbed a staircase (state 4) for 22 seconds.

The present invention makes it possible, at reduced cost, to determine the walking activity of a person with improved accuracy.

The invention claimed is:

1. A system for observing a walking activity of a person, comprising:
    a device comprising one or more of a magnetometer, an accelerometer, and a gyrometer, for delivering at output, for a footstep of the person:
        a first difference of angular speeds of a corresponding tibia between an instant at which a heel of a foot is planted and an instant at which the foot is laid flat,
        a second difference of angular speeds of the corresponding tibia between the instant at which the heel of the foot is planted and an instant at which a last toe of the foot is lifted, and
        an angular speed of the corresponding tibia at the instant at which the foot is laid flat;
    said system further comprising an analysis module communicatively coupled to the device, the analysis module comprising a processor configured to analyze signals delivered by the device and to determine, only from an analysis of these signals, a type of walking of the user as a function of time by using a hidden Markov model with N states corresponding respectively to N types of walking;
    wherein:
    a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{\frac{-(\underline{x}(n)-\underline{\mu})^T \Sigma^{-1}(\underline{x}(n)-\underline{\mu})}{2}}$$

in which:
        $\underline{x}(n)$ represents a column vector with components of three signals transmitted by the device;
        $\underline{\mu}$ represents a column vector with three components $\mu_1$, $\mu_2$, $\mu_3$, representative of the state of the hidden Markov model corresponding to said type of walking; and
        $|\Sigma|$ represents an absolute value of a determinant of a diagonal matrix $\Sigma$ of dimension 3 representative of the state of the hidden Markov model corresponding to said type of walking;
    the probability density of correspondence between the signals delivered by the device and the state of the hidden Markov model representing the type of walking is defined by a linear combination of said first expressions for probability densities of the set of types of walking, a sum of the coefficients of said linear combination being equal to 1;
    the analysis module is further configured to determine the type of walking of the user from among a set of at least two types of walking comprising walking on a flat surface, walking down a descent, walking up a climb, climbing a staircase, and descending a staircase; and
    for walking on the flat surface, the three components $\mu_1$, $\mu_2$, $\mu_3$ of the column vector $\underline{\mu}$ are such that $\mu_1 \in [-1.2; -1]$, $\mu_2 \in [0.25; 0.35]$, and $\mu_3 \in [-0.3; -0.2]$, and three diagonal components $\Sigma_1$, $\Sigma_2$, $\Sigma_3$ of the diagonal matrix $\Sigma$ are such that $\Sigma_1 \in [10^{-3}; 510^{-2}]$, $\Sigma_2 \in [10^{-4}; 510^{-3}]$, and $\Sigma_3 \in [10^{-4}; 510^{-2}]$.

2. The system as claimed in claim 1, wherein probabilities P, of said hidden Markov model, of switching between two states representing respectively one of said types of walking are such that:
    $P(state_i, state_j) \in [0.5; 0.9999]$, when i is different from j; and
    $P(state_i, state_j) \in [0; 0.5]$, when i is equal to j.

3. The system as claimed in claim 1, wherein said analysis module is fastened or remote with respect to the device, and the device comprises wired or wireless transmission means for transmitting its measurements to said analysis module.

4. The system as claimed in claim 1, further comprising a display fastened to the device or a remote display.

5. A system for observing a walking activity of a person, comprising:
    a device comprising one or more of a magnetometer, an accelerometer, and a gyrometer, for delivering at output, for a footstep of the person:
        a first difference of angular speeds of a corresponding tibia between an instant at which a heel of a foot is planted and an instant at which the foot is laid flat,
        a second difference of angular speeds of the corresponding tibia between the instant at which the heel of the foot is planted and an instant at which a last toe of the foot is lifted, and
        an angular speed of the corresponding tibia at the instant at which the foot is laid flat;
    said system further comprising an analysis module communicatively coupled to the device, the analysis module comprising a processor configured to analyze signals delivered by the device and to determine, only from an analysis of these signals, a type of walking of the user as a function of time by using a hidden Markov model with N states corresponding respectively to N types of walking;
    wherein:
    a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{\frac{-(\underline{x}(n)-\underline{\mu})^T \Sigma^{-1}(\underline{x}(n)-\underline{\mu})}{2}}$$

in which:
        $\underline{x}(n)$ represents a column vector with components of three signals transmitted by the device;
        $\underline{\mu}$ represents a column vector with three components $\mu_1$, $\mu_2$, $\mu_3$, representative of the state of the hidden Markov model corresponding to said type of walking; and

|Σ| represents an absolute value of a determinant of a diagonal matrix Σ of dimension 3 representative of the state of the hidden Markov model corresponding to said type of walking;

the probability density of correspondence between the signals delivered by the device and the state of the hidden Markov model representing the type of walking is defined by a linear combination of said first expressions for probability densities of the set of types of walking, a sum of the coefficients of said linear combination being equal to 1;

the analysis module is further configured to determine the type of walking of the user from among a set of at least two types of walking comprising walking on a flat surface, walking down a descent, walking up a climb, climbing a staircase, and descending a staircase; and for walking down a descent, the three components $\mu_1, \mu_2, \mu_3$ of the column vector $\underline{\mu}$ are such that $\mu_1 \in [-1.4; -1]$, $\mu_2 \in [0.05; 0.25]$, and $\mu_3 \in [-0.7; -0.2]$, and three diagonal components $\Sigma_1, \Sigma_2, \Sigma_3$ of the diagonal matrix Σ are such that $\Sigma_1 \in [10^{-3}; 510^{-2}]$, $\Sigma_2 \in [10^{-3}; 10^{-2}]$, and $\Sigma_3 \in [10^{-4}; 510^{-2}]$.

6. The system as claimed in claim 5, wherein probabilities P, of said hidden Markov model, of switching between two states representing respectively one of said types of walking are such that:

P(state$_i$,state$_j$)∈[0.5; 0.9999], when i is different from j; and

P(state$_i$,state$_j$)∈0; 0.51, when i is equal to j.

7. The system as claimed in claim 5, wherein said analysis module is fastened or remote with respect to the device, and the device comprises wired or wireless transmission means for transmitting its measurements to said analysis module.

8. The system as claimed in claim 5, further comprising a display fastened to the device or a remote display.

9. A system for observing a walking activity of a person, comprising:

a device comprising one or more of a magnetometer, an accelerometer, and a gyrometer, for delivering at output, for a footstep of the person:
  a first difference of angular speeds of a corresponding tibia between an instant at which a heel of a foot is planted and an instant at which the foot is laid flat,
  a second difference of angular speeds of the corresponding tibia between the instant at which the heel of the foot is planted and an instant at which a last toe of the foot is lifted, and
  an angular speed of the corresponding tibia at the instant at which the foot is laid flat;

said system further comprising an analysis module communicatively coupled to the device, the analysis module comprising a processor configured to analyze signals delivered by the device and to determine, only from an analysis of these signals, a type of walking of the user as a function of time by using a hidden Markov model with N states corresponding respectively to N types of walking;

wherein:

a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{-\frac{(\underline{x}(n)-\underline{\mu})^T \Sigma^{-1} (\underline{x}(n)-\underline{\mu})}{2}}$$

in which:
  $\underline{x}(n)$ represents a column vector with components of three signals transmitted by the device;
  $\underline{\mu}$ represents a column vector with three components $\mu_1, \mu_2, \mu_3$, representative of the state of the hidden Markov model corresponding to said type of walking; and
  |Σ| represents an absolute value of a determinant of a diagonal matrix Σ of dimension 3 representative of the state of the hidden Markov model corresponding to said type of walking;

the probability density of correspondence between the signals delivered by the device and the state of the hidden Markov model representing the type of walking is defined by a linear combination of said first expressions for probability densities of the set of types of walking, a sum of the coefficients of said linear combination being equal to 1;

the analysis module is further configured to determine the type of walking of the user from among a set of at least two types of walking comprising walking on a flat surface, walking down a descent, walking up a climb, climbing a staircase, and descending a staircase; and for walking up a climb, the three components $\mu_1, \mu_2, \mu_3$ of the column vector $\underline{\mu}$ are such that $\mu_1 \in [-1.1; -0.2]$, $\mu_2 \in [0.1; 0.2]$, and $\mu_3 \in [-1.2; -0.6]$, and three diagonal components $\Sigma_1, \Sigma_2, \Sigma_3$ of the diagonal matrix Σ are such that $\Sigma_1 \in [10^{-3}; 510^{-2}]$, $\Sigma_2 \in [10^{-3}; 10^{-2}]$, and $\Sigma_3 \in [10^{-3}; 510^{-2}]$.

10. The system as claimed in claim 9, wherein probabilities P, of said hidden Markov model, of switching between two states representing respectively one of said types of walking are such that:

P(state$_i$,state$_j$)∈[0.5; 0.9999], when i is different from j; and

P(state$_i$,state$_j$)∈[0; 0.5], when i is equal to j.

11. The system as claimed in claim 9, wherein said analysis module is fastened or remote with respect to the device, and the device comprises wired or wireless transmission means for transmitting its measurements to said analysis module.

12. The system as claimed in claim 9, further comprising a display fastened to the device or a remote display.

13. A system for observing a walking activity of a person, comprising:

a device comprising one or more of a magnetometer, an accelerometer, and a pyrometer, for delivering at output, for a footstep of the person:
  a first difference of angular speeds of a corresponding tibia between an instant at which a heel of a foot is planted and an instant at which the foot is laid flat,
  a second difference of angular speeds of the corresponding tibia between the instant at which the heel of the foot is planted and an instant at which a last toe of the foot is lifted, and
  an angular speed of the corresponding tibia at the instant at which the foot is laid flat;

said system further comprising an analysis module communicatively coupled to the device, the analysis module comprising a processor configured to analyse-analyze signals delivered by the device and to determine, only from an analysis of these signals, a type of walking of the user as a function of time by using a hidden Markov model with N states corresponding respectively to N types of walking;

wherein:

a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{\frac{-(\underline{x}(n)-\underline{\mu})^T \Sigma^{-1}(\underline{x}(n)-\underline{\mu})}{2}}$$

in which:
- $\underline{x}(n)$ represents a column vector with components of three signals transmitted by the device;
- $\underline{\mu}$ represents a column vector with three components $\mu_1$, $\mu_2$, $\mu_3$, representative of the state of the hidden Markov model corresponding to said type of walking; and
- $|\Sigma|$ represents an absolute value of a determinant of a diagonal matrix $\Sigma$ of dimension 3 representative of the state of the hidden Markov model corresponding to said type of walking;

the probability density of correspondence between the signals delivered by the device and the state of the hidden Markov model representing the type of walking is defined by a linear combination of said first expressions for probability densities of the set of types of walking, a sum of the coefficients of said linear combination being equal to 1;

the analysis module is further configured to determine the type of walking of the user from among a set of at least two types of walking comprising walking on a flat surface, walking down a descent, walking up a climb, climbing a staircase, and descending a staircase; and for climbing a staircase, the three components $\mu_1, \mu_2, \mu_3$ of the column vector $\underline{\mu}$ are such that $\mu_1 \in [-0.4; -0.15]$, $\mu_2 \in [0; 0.2]$, and $\mu_3 \in [-0.7; -0.4]$, and three diagonal components $\Sigma_1, \Sigma_2, \Sigma_3$ of the diagonal matrix $\Sigma$ are such that $\Sigma_1 \in [10^{-2}; 10^{-1}]$, $\Sigma_2 \in [510^{-3}; 510^{-2}]$, and $\Sigma_3 \in [10^{-2}; 10^{-1}]$.

14. The system as claimed in claim 13, wherein probabilities P, of said hidden Markov model, of switching between two states representing respectively one of said types of walking are such that:

P(state$_i$,state$_j$)$\in[0.5; 0.9999]$, when i is different from j; and
P(state$_i$,state$_j$)$\in[0; 0.5]$, when i is equal to j.

15. The system as claimed in claim 13, wherein said analysis module is fastened or remote with respect to the device, and the device comprises wired or wireless transmission means for transmitting its measurements to said analysis module.

16. The system as claimed in claim 13, further comprising a display fastened to the device or a remote display.

17. A system for observing a walking activity of a person, comprising:

a device comprising one or more of a magnetometer, an accelerometer, and a gyrometer, for delivering at output, for a footstep of the person:
- a first difference of angular speeds of a corresponding tibia between an instant at which a heel of a foot is planted and an instant at which the foot is laid flat,
- a second difference of angular speeds of the corresponding tibia between the instant at which the heel of the foot is planted and an instant at which a last toe of the foot is lifted, and
- an angular speed of the corresponding tibia at the instant at which the foot is laid flat;

said system further comprising an analysis module communicatively coupled to the device, the analysis module comprising a processor configured to analyze signals delivered by the device and to determine, only from an analysis of these signals, a type of walking of the user as a function of time by using a hidden Markov model with N states corresponding respectively to N types of walking;

wherein:

a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{\frac{-(\underline{x}(n)-\underline{\mu})^T \Sigma^{-1}(\underline{x}(n)-\underline{\mu})}{2}}$$

in which:
- $\underline{x}(n)$ represents a column vector with components of three signals transmitted by the device;
- $\underline{\mu}$ represents a column vector with three components $\mu_1$, $\mu_2$, $\mu_3$, representative of the state of the hidden Markov model corresponding to said type of walking; and
- $|\Sigma|$ represents an absolute value of a determinant of a diagonal matrix $\Sigma$ of dimension 3 representative of the state of the hidden Markov model corresponding to said type of walking;

the probability density of correspondence between the signals delivered by the device and the state of the hidden Markov model representing the type of walking is defined by a linear combination of said first expressions for probability densities of the set of types of walking, a sum of the coefficients of said linear combination being equal to 1;

the analysis module is further configured to determine the type of walking of the user from among a set of at least two types of walking comprising walking on a flat surface, walking down a descent, walking up a climb, climbing a staircase, and descending a staircase; and for descending a staircase, the three components $\mu_1, \mu_2, \mu_3$ of the column vector $\underline{\mu}$ are such that $\mu_1 \in [-0.8; -0.6]$, $\mu_2 \in [-0.3; -0.1]$, and $\mu_3 \in [-0.4; -0.25]$, and three diagonal components $\Sigma_1, \Sigma_2, \Sigma_3$ of the diagonal matrix $\Sigma$ are such that $\Sigma_1 \in [10^{-3}; 10^{-2}]$, $\Sigma_2 \in [10^{-4}; 10^{-3}]$, and $\Sigma_3 \in [10^{-4}; 10^{-3}]$.

18. The system as claimed in claim 17, wherein probabilities P, of said hidden Markov model, of switching between two states representing respectively one of said types of walking are such that:

P(state$_i$,state$_j$)$\in[0.5; 0.9999]$, when i is different from j; and
P(state$_i$,state$_j$)$\in[0; 0.5]$, when i is equal to j.

19. The system as claimed in claim 17, wherein said analysis module is fastened or remote with respect to the device, and the device comprises wired or wireless transmission means for transmitting its measurements to said analysis module.

20. The system as claimed in claim 17, further comprising a display fastened to the device or a remote display.

21. A method for observing a walking activity of a person, based on, during a footstep, signals representing a first difference of angular speeds of a corresponding tibia between an instant at which a heel of a foot is planted and an instant at which the foot is laid flat, a second difference of angular speeds of the corresponding tibia between the instant at which the heel of the foot is planted and an instant at which a last toe of the foot is lifted, and an angular speed of the corresponding tibia at the instant at which the foot is laid flat, said signals being provided as an output of a device comprising one or more of a magnetometer, an accelerometer, and a gyrometer,
wherein a computing device is used to analyse said signals to determine a type of walking of the user as a function of time by using a hidden Markov model with N states corresponding respectively to N types of walking, and wherein:
a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{-\frac{(\underline{x}(n)-\underline{\mu})^T \Sigma^{-1}(\underline{x}(n)-\underline{\mu})}{2}}$$

in which:
$\underline{x}(n)$ represents a column vector with components of three signals transmitted by the device;
$\underline{\mu}$ represents a column vector with three components $\mu_1$, $\mu_2$, $\mu_3$, representative of the state of the hidden Markov model corresponding to said type of walking; and
$|\Sigma|$ represents an absolute value of a determinant of a diagonal matrix $\Sigma$ of dimension 3 representative of the state of the hidden Markov model corresponding to said type of walking;
the probability density of correspondence between the signals delivered by the device and the state of the hidden Markov model representing the type of walking is defined by a linear combination of said first expressions for probability densities of the set of types of walking, a sum of the coefficients of said linear combination being equal to 1;
the type of walking of the user is determined from among a set of at least two types of walking comprising walking on a flat surface, walking down a descent, walking up a climb, climbing a staircase, and descending a staircase; and
for walking on the flat surface, the three components $\mu_1$, $\mu_2$, $\mu_3$ of the column vector $\underline{\mu}$ are such that $\mu_1 \in [-1.2; -1]$, $\mu_2 \in [0.25; 0.35]$, and $\mu_3 \in [-0.3; -0.2]$, and three diagonal components $\Sigma_1$, $\Sigma_2$, $\Sigma_3$ of the diagonal matrix $\Sigma$ are such that $\Sigma_1 \in [10^{-3}; 510^{-2}]$, $\Sigma_2 \in [10^{-4}; 510^{-3}]$, and $\Sigma_3 \in [10^{-4}; 510^{-2}]$.

22. A method for observing a walking activity of a person, based on, during a footstep, signals representing a first difference of angular speeds of a corresponding tibia between an instant at which a heel of a foot is planted and an instant at which the foot is laid flat, a second difference of angular speeds of the corresponding tibia between the instant at which the heel of the foot is planted and an instant at which a last toe of the foot is lifted, and an angular speed of the corresponding tibia at the instant at which the foot is laid flat, said signals being provided as an output of a device comprising one or more of a magnetometer, an accelerometer, and a gyrometer,
wherein a computing device is used to analyse said signals to determine a type of walking of the user as a function of time by using a hidden Markov model with N states corresponding respectively to N types of walking, and wherein:
a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{-\frac{(\underline{x}(n)-\underline{\mu})^T \Sigma^{-1}(\underline{x}(n)-\underline{\mu})}{2}}$$

in which:
$\underline{x}(n)$ represents a column vector with components of three signals transmitted by the device;
$\underline{\mu}$ represents a column vector with three components $\mu_1$, $\mu_2$, $\mu_3$, representative of the state of the hidden Markov model corresponding to said type of walking; and
$|\Sigma|$ represents an absolute value of a determinant of a diagonal matrix $\Sigma$ of dimension 3 representative of the state of the hidden Markov model corresponding to said type of walking;
the probability density of correspondence between the signals delivered by the device and the state of the hidden Markov model representing the type of walking is defined by a linear combination of said first expressions for probability densities of the set of types of walking, a sum of the coefficients of said linear combination being equal to 1;
the type of walking of the user is determined from among a set of at least two types of walking comprising walking on a flat surface, walking down a descent, walking up a climb, climbing a staircase, and descending a staircase; and
for walking down a descent, the three components $\mu_1$, $\mu_2$, $\mu_3$ of the column vector $\underline{\mu}$ are such that $\mu_1 \in [-1.4; -1]$, $\mu_2 \in [0.05; 0.25]$, and $\mu_3 \in [-0.7; -0.2]$, and three diagonal components $\Sigma_1$, $\Sigma_2$, $\Sigma_3$ of the diagonal matrix $\Sigma$ are such that $\Sigma_1 \in [10^{-3}; 510^{-2}]$, $\Sigma_2 \in [10^{-3}; 10^{-2}]$, and $\Sigma_3 \in [10^{-4}; 510^{-2}]$.

23. A method for observing a walking activity of a person, based on, during a footstep, signals representing a first difference of angular speeds of a corresponding tibia between an instant at which a heel of a foot is planted and an instant at which the foot is laid flat, a second difference of angular speeds of the corresponding tibia between the instant at which the heel of the foot is planted and an instant at which a last toe of the foot is lifted, and an angular speed of the corresponding tibia at the instant at which the foot is laid flat, said signals being provided as an output of a device comprising one or more of a magnetometer, an accelerometer, and a gyrometer,
wherein a computing device is used to analyse said signals to determine a type of walking of the user as a function of time by using a hidden Markov model with N states corresponding respectively to N types of walking, and wherein:
a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{-\frac{(\underline{x}(n)-\underline{\mu})^T \Sigma^{-1}(\underline{x}(n)-\underline{\mu})}{2}}$$

in which:
$\underline{x}(n)$ represents a column vector with components of three signals transmitted by the device;
$\underline{\mu}$ represents a column vector with three components $\mu_1$, $\mu_2$, $\mu_3$, representative of the state of the hidden Markov model corresponding to said type of walking; and

|Σ| represents an absolute value of a determinant of a diagonal matrix Σ of dimension 3 representative of the state of the hidden Markov model corresponding to said type of walking;

the probability density of correspondence between the signals delivered by the device and the state of the hidden Markov model representing the type of walking is defined by a linear combination of said first expressions for probability densities of the set of types of walking, a sum of the coefficients of said linear combination being equal to 1;

the type of walking of the user is determined from among a set of at least two types of walking comprising walking on a flat surface, walking down a descent, walking up a climb, climbing a staircase, and descending a staircase; and for walking up a climb, the three components $\mu_1, \mu_2, \mu_3$ of the column vector $\underline{\mu}$ are such that $\mu_1 \in [-1.1; -0.2]$, $\mu_2 \in [0.1; 0.2]$, and $\mu_3 \in [-1.2; -0.6]$, and three diagonal components $\Sigma_1, \Sigma_2, \Sigma_3$ of the diagonal matrix Σ are such that $\Sigma_1 \in [10^{-3}; 510^{-2}]$, $\Sigma_2 \in [10^{-3}; 10^{-2}]$, and $\Sigma_3 \in [10^{-3}; 510^{-2}]$.

24. A method for observing a walking activity of a person, based on, during a footstep, signals representing a first difference of angular speeds of a corresponding tibia between an instant at which a heel of a foot is planted and an instant at which the foot is laid flat, a second difference of angular speeds of the corresponding tibia between the instant at which the heel of the foot is planted and an instant at which a last toe of the foot is lifted, and an angular speed of the corresponding tibia at the instant at which the foot is laid flat, said signals being provided as an output of a device comprising one or more of a magnetometer, an accelerometer, and a gyrometer, wherein a computing device is used to analyse said signals to determine a type of walking of the user as a function of time by using a hidden Markov model with N states corresponding respectively to N types of walking, and wherein:

a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{\frac{-(\underline{x}(n)-\underline{\mu})^T \Sigma^{-1} (\underline{x}(n)-\underline{\mu})}{2}}$$

in which:
$\underline{x}(n)$ represents a column vector with components of three signals transmitted by the device;
$\underline{\mu}$ represents a column vector with three components $\mu_1, \mu_2, \mu_3$, representative of the state of the hidden Markov model corresponding to said type of walking; and
|Σ| represents an absolute value of a determinant of a diagonal matrix Σ of dimension 3 representative of the state of the hidden Markov model corresponding to said type of walking;

the probability density of correspondence between the signals delivered by the device and the state of the hidden Markov model representing the type of walking is defined by a linear combination of said first expressions for probability densities of the set of types of walking, a sum of the coefficients of said linear combination being equal to 1;

the type of walking of the user is determined from among a set of at least two types of walking comprising walking on a flat surface, walking down a descent, walking up a climb, climbing a staircase, and descending a staircase; and for climbing a staircase, the three components $\mu_1, \mu_2, \mu_3$ of the column vector $\underline{\mu}$ are such that $\mu_1 \in [-0.4; -0.15]$, $\mu_2 \in [0; 0.2]$, and $\mu_3 \in [-0.7; -0.4]$, and three diagonal components $\Sigma_1, \Sigma_2, \Sigma_3$ of the diagonal matrix Σ are such that $\Sigma_1 \in [10^{-2}; 10^{-1}]$, $\Sigma_2 \in [510^{-3}; 510^{-2}]$, and $\Sigma_3 \in [10^{-2}; 10^{-1}]$.

25. A method for observing a walking activity of a person, based on, during a footstep, signals representing a first difference of angular speeds of a corresponding tibia between an instant at which a heel of a foot is planted and an instant at which the foot is laid flat, a second difference of angular speeds of the corresponding tibia between the instant at which the heel of the foot is planted and an instant at which a last toe of the foot is lifted, and an angular speed of the corresponding tibia at the instant at which the foot is laid flat, said signals being provided as an output of a device comprising one or more of a magnetometer, an accelerometer, and a gyrometer, wherein a computing device is used to analyse said signals to determine a type of walking of the user as a function of time by using a hidden Markov model with N states corresponding respectively to N types of walking, and wherein:

a probability density $p_x(\underline{x}(n))$ of correspondence between the signals delivered by the device and a state of the hidden Markov model representing a type of walking is defined by the following first expression:

$$\frac{1}{\sqrt{2\pi|\Sigma|}} \cdot e^{\frac{-(\underline{x}(n)-\underline{\mu})^T \Sigma^{-1} (\underline{x}(n)-\underline{\mu})}{2}}$$

in which:
$\underline{x}(n)$ represents a column vector with components of three signals transmitted by the device;
$\underline{\mu}$ represents a column vector with three components $\mu_1, \mu_2, \mu_3$, representative of the state of the hidden Markov model corresponding to said type of walking; and
|Σ| represents an absolute value of a determinant of a diagonal matrix Σ of dimension 3 representative of the state of the hidden Markov model corresponding to said type of walking;

the probability density of correspondence between the signals delivered by the device and the state of the hidden Markov model representing the type of walking is defined by a linear combination of said first expressions for probability densities of the set of types of walking, a sum of the coefficients of said linear combination being equal to 1;

the type of walking of the user is determined from among a set of at least two types of walking comprising walking on a flat surface, walking down a descent, walking up a climb, climbing a staircase, and descending a staircase; and for descending a staircase, the three components $\mu_1, \mu_2, \mu_3$ of the column vector $\underline{\mu}$ are such that $\mu_1 \in [-0.8; -0.6]$, $\mu_2 \in [-0.3; -0.1]$, and $\mu_3 \in [-0.4; -0.25]$, and three diagonal components $\Sigma_1, \Sigma_2, \Sigma_3$ of the diagonal matrix Σ are such that $\Sigma_1 \in [10^{-3}; 10^{-2}]$, $\Sigma_2 \in [10^{-4}; 10^{-3}]$, and $\Sigma_3 \in [10^{-4}; 10^{-3}]$.

* * * * *